United States Patent [19]

Semler et al.

[11] Patent Number: 5,304,186
[45] Date of Patent: Apr. 19, 1994

[54] ARTERY CLAMP

[76] Inventors: Herbert J. Semler; Shirley L. Semler, both of 9155 SW. Barnes Rd., Portland, Oreg. 97225; Richard N. Meyer, 2076 SE. Hanover Ct., Hillsboro, Oreg. 97123

[21] Appl. No.: 903,528

[22] Filed: Jun. 23, 1992

[51] Int. Cl.⁵ ............................................. A61B 17/12
[52] U.S. Cl. ..................................... 606/151; 606/201
[58] Field of Search ............... 606/201, 151; 248/124, 248/125, 507, 295.1, 298

[56] References Cited

U.S. PATENT DOCUMENTS

| | | | |
|---|---|---|---|
| 1,397,453 | 11/1921 | Rekar | 248/125 |
| 3,625,219 | 12/1971 | Abrams . | |
| 3,779,249 | 12/1973 | Semler . | |
| 4,233,980 | 11/1980 | McRae et al. . | |
| 4,572,182 | 2/1986 | Royse . | |
| 4,742,825 | 5/1988 | Freund et al. . | |

Primary Examiner—Michael H. Thaler
Attorney, Agent, or Firm—Kolisch, Hartwell, Dickinson, McCormack & Heuser

[57] ABSTRACT

The artery clamp of the invention includes a base which has an elongate rod mounted normal thereto. An elongate sleeve having a central bore is carried on the rod. The sleeve includes a channel which extends the length thereof, which channel has an axially extending slot along at least a portion of its length. The rod is received in the central bore to allow rotation of the sleeve relative to the base of the artery clamp. An arm structure extends laterally outwardly from the sleeve and includes an extensible portion which is laterally adjustable relative to the sleeve and which includes a mechanism for carrying a pressure pad thereon.

16 Claims, 4 Drawing Sheets

ARTERY CLAMP

TECHNICAL FIELD

This invention relates to artery clamps, and specifically to an improved artery clamp which allows for three dimensional adjustment of a pressure pad relative to a patient undergoing a catheterization procedure.

BACKGROUND ART

Catheterization procedures require that a large blood vessel, generally the femoral artery in a patient's groin area, be punctured and a catheter introduced therein. Such a catheter may be used as part of an angioplasty procedure, or for other procedures in which blood vessels have instruments directed therein. The artery clamp of the invention comes into use at the end of the catheterization procedure when the catheter and associated components are removed from the blood vessel when it is necessary to stop the flow of blood from a relatively large puncture of the blood vessel.

A variety of artery clamps are known. One such artery clamp is disclosed in U.S. Pat. No. 3,779,249 to Semler for ARTERY CLAMP. The early artery clamp allows only vertical movement of an arm carrying a pressure pad thereon. It is therefore necessary to shift the base of the artery clamp in order to laterally position the pressure pad over the puncture site created during the catheterization procedure. An important feature of the Semler Artery Clamp is the provision of pressure feedback to a medical technician positioning the clamp. As the pressure pad is brought into contact with the patient's body over the puncture site, the technician has a feel for how much pressure is being applied as a result of manually lowering the arm of the artery clamp into place. Quite simply, the greater the downward pressure needed to move the arm, the greater the pressure that is exerted on the patient.

Another form of artery clamp is disclosed in U.S. Pat. No. 4,233,980 to McCray et al. This clamp provides for three dimensional movement of the pressure pad relative to the base while relying on a rubber sleeve carried inside the arm to maintain the vertical position of the arm.

Another artery clamp is disclosed in U.S. Pat. No. 4,742,825 to Freund et al., which provides three dimensional movement of a pad-bearing arm and which provides a threaded pad mount for exerting pressure on a pad.

As the occurrence of catheterization procedures becomes more frequent, the use of artery clamps becomes more commonplace. It is desired that such clamps be of simple construction and that they not have an excessive number of exposed parts which will collect serum and tissue from the patient's on which they are used.

DISCLOSURE OF THE INVENTION

An object of the invention is to provide an artery clamp which will allow placement of an artery pressure pad, carried on the clamp, in three dimensions relative to a patient and the base of the clamp.

Another object of the invention is to provide an artery clamp which provides a pressure feedback to a medical technician indicating the amount of pressure being applied to a patient.

A further object of the invention is to provide an artery clamp which contains mechanisms for locking an arm, both vertically and horizontally, of the artery clamp in a desired position.

Still another object of the invention is to provide an artery clamp which contains an indexing mechanism in order to track relative pressure applied to a patient over a period of time.

The artery clamp of the invention includes a base which has an elongate rod mounted normal thereto. An elongate sleeve having a central bore is carried on the rod. The sleeve includes a channel which extends the length thereof, which channel has an axially extending slot along at least a portion of its length. The rod is received in the central bore to allow rotation of the sleeve relative to the base of the artery clamp. An arm structure extends laterally outwardly from the sleeve and includes an extensible portion which is laterally adjustable relative to the sleeve and which includes a mechanism for carrying a pressure pad thereon.

These and other objects and advantages of the invention will become more fully apparent as the description which follows is read in conjunction with the drawings.

BEST MODE FOR CARRYING OUT THE INVENTION

Figure 1:
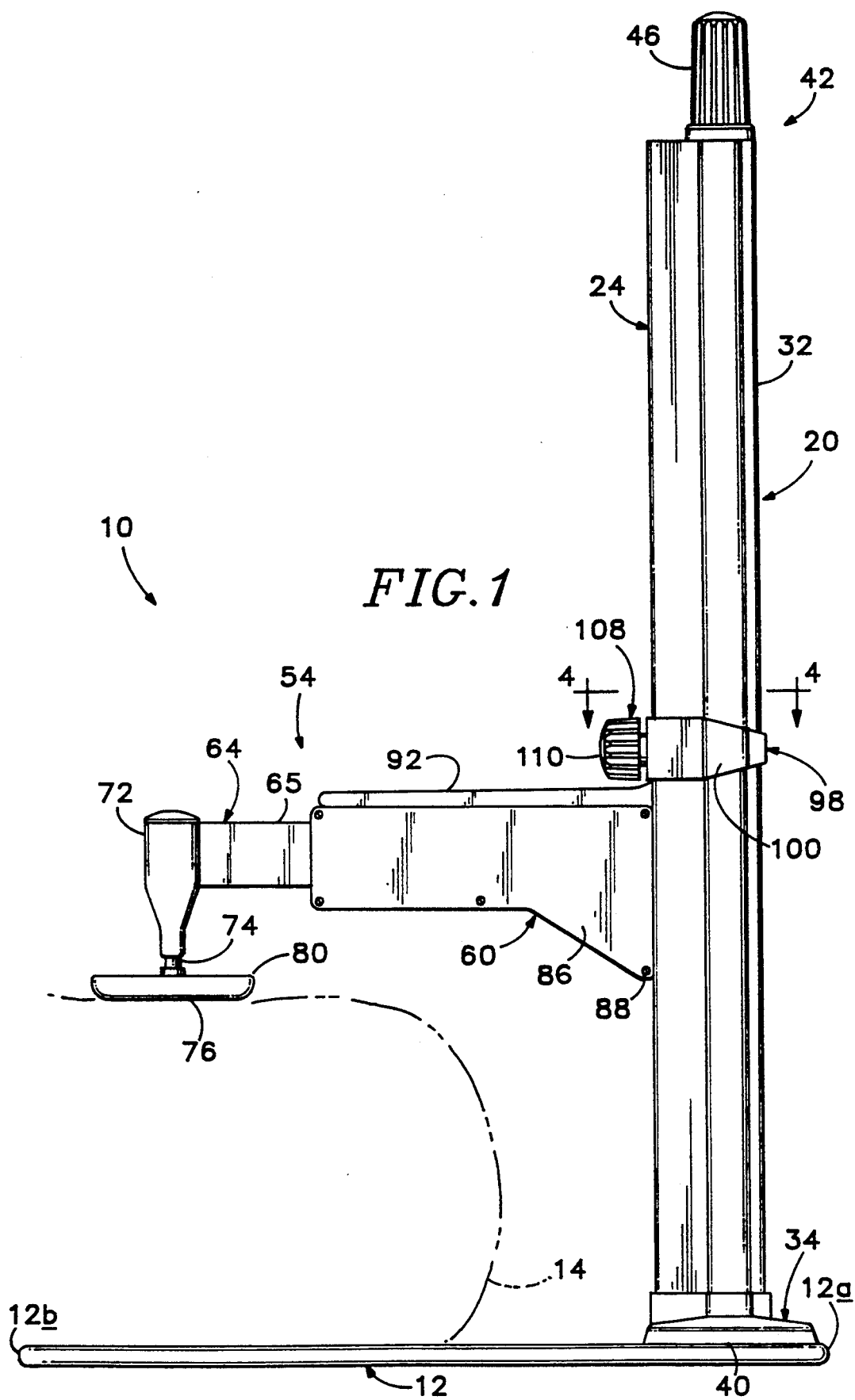
FIG. 1 is a side elevation of the artery clamp of the invention.
Figure 2:
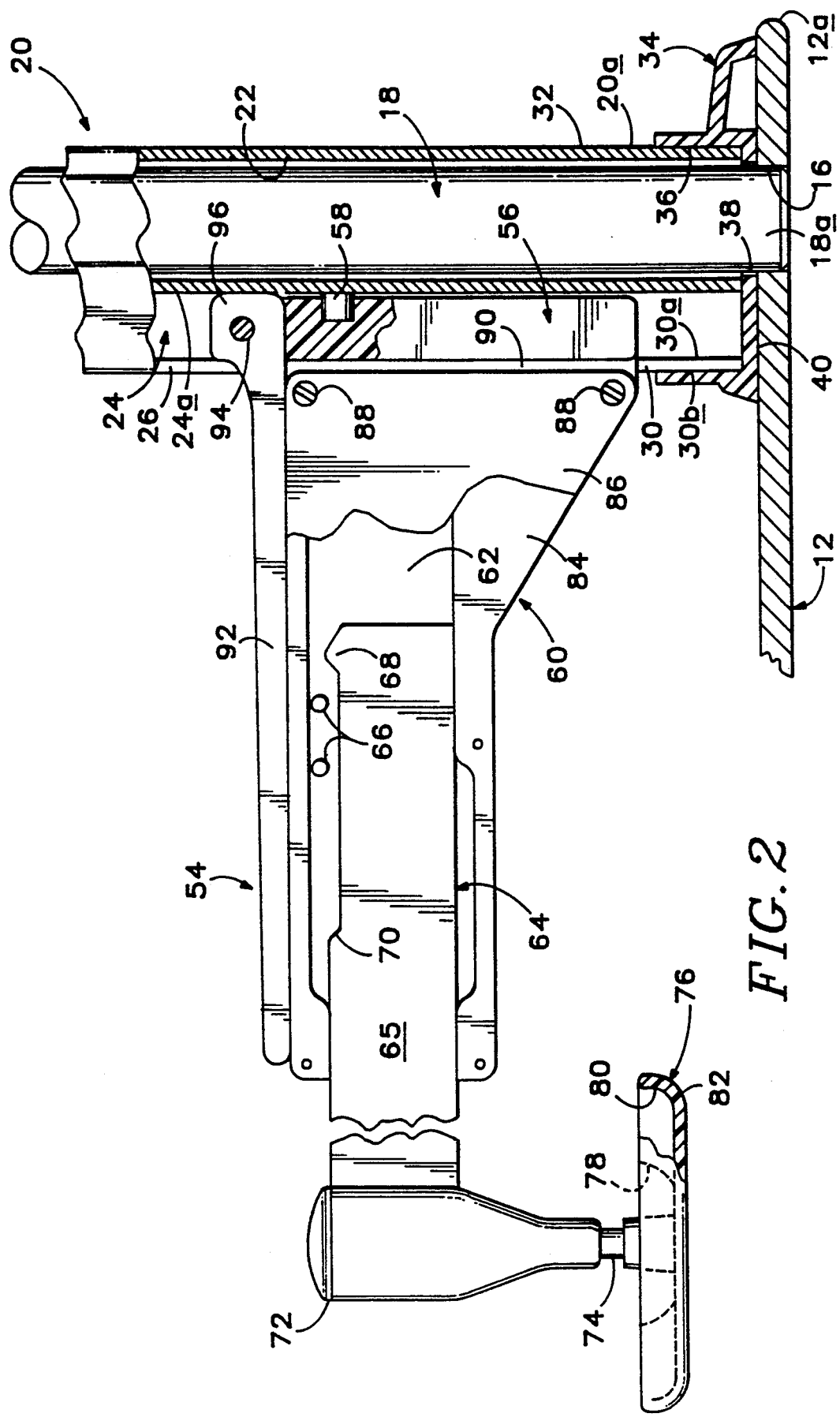
FIG. 2 is an enlarged side elevation of an arm structure of the invention, with portions broken away to show interior detail.
Figure 3:
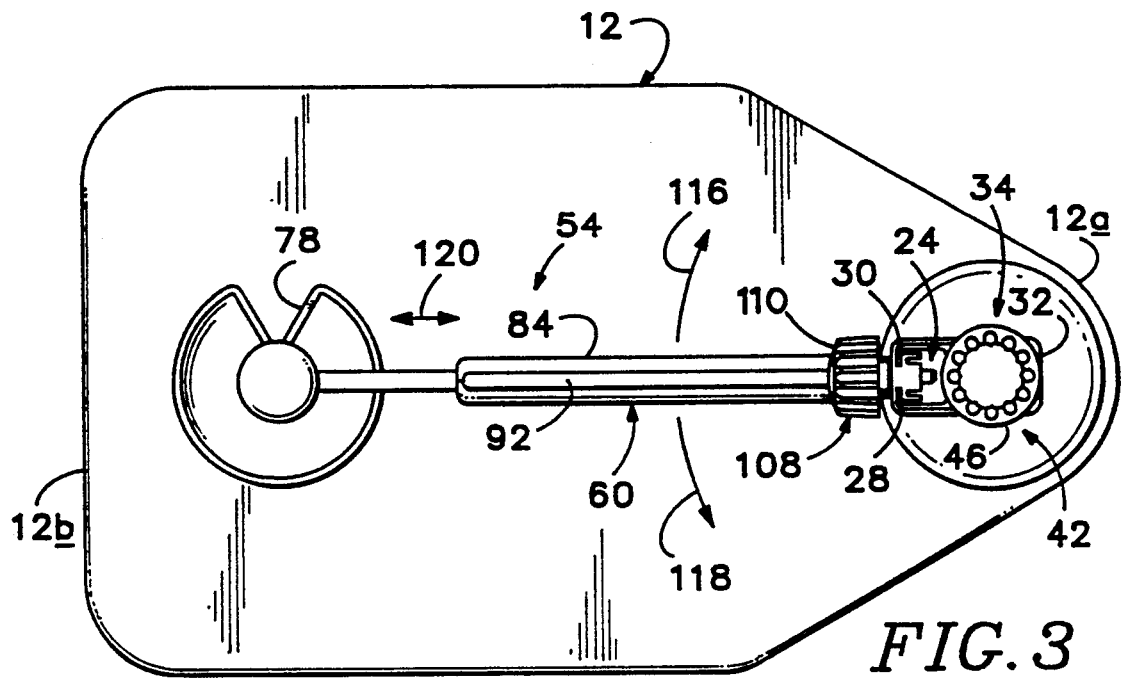
FIG. 3 is a top plan view of the artery clamp of FIG. 1.
Figure 4:
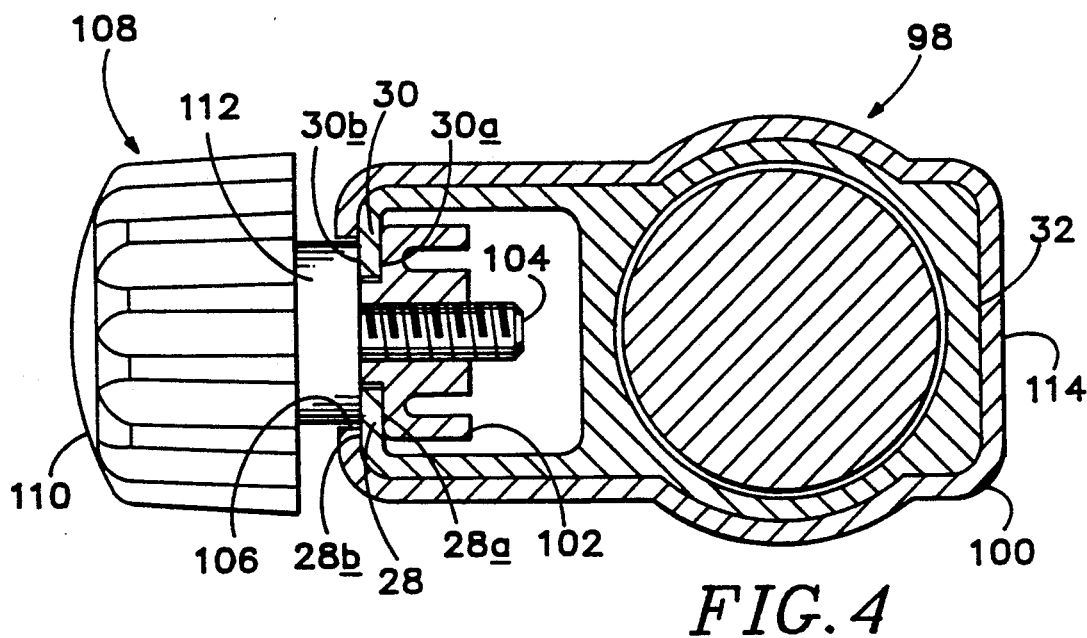
FIG. 4 is an enlarged top plan section through the rod and sleeve of the invention, taken generally along the line 4—4 of FIG. 1.

Referring now to the drawings, and initially to FIGS. 1, 2 and 3, an improved artery clamp constructed according to the invention is depicted generally at 10. Artery clamp 10 includes a base 12, which is a generally planar structure and which has a narrowed area at one end 12a thereof. In the preferred embodiment, end 12a may be thought of as having a generally triangular form. The other end 12b of base 12 has a generally rectangular form. The corners of the base are rounded to provide a smooth surface as the base is inserted beneath a patient, shown in phantom at 14. In use, artery clamp 10 is positioned with base 12 beneath the patient's thigh or, in some instances, beneath a mattress pad on which the patient is reclined.

Base 12 includes a bore 16 located adjacent end 12a thereof. An elongate rod 18 is compression fit into bore 16, in the preferred embodiment, such that rod 18 is mounted normal to base 12, with one end 18a received in bore 16. Alternate embodiments of artery clamp 10 may include a threaded fastener of some form extending through base 12 and into rod 18.

A sleeve 20 is provided and includes a central bore 22 which extends the length of sleeve 20 and which is constructed and arranged to receive rod 18 therein. Sleeve 20 is constructed to completely encase rod 18 and to be rotatable thereon.

A channel 24 is provided in sleeve 20 and extends the length of the sleeve. A slot 26 extends axially along channel 24 for at least a portion of its length, and in the preferred embodiment, extends the entire length of the channel. Slot 26 is surrounded by a pair of flanges 28, 30 each of which has an interior surface, 28a, 30a, and an exterior surface 28b, 30b, respectively. Channel 24 has a interior rear wall 24a, which is located between channel 24 and central bore 22.

An index plate 32 is provided on sleeve 20 opposite slot 26. Index plate 32 includes indicia thereon, which indicia may take the form of English or metric measurements, or some arbitrary index system.

A bushing 34 is provided at the base, or one end 20a of sleeve 20 and is press or friction fit on the outside of the sleeve. Bushing 34 has a sleeve-receiving region 36 for receiving one end of the sleeve therein. A bore 38 extends through the bottom of bushing 34 and is sized to allow passage around rod 18. Bushing 34 has a flat lower surface 40 which contacts base 12. Bushing 34 rotates with sleeve 20 relative to base 12.

Figure 5:
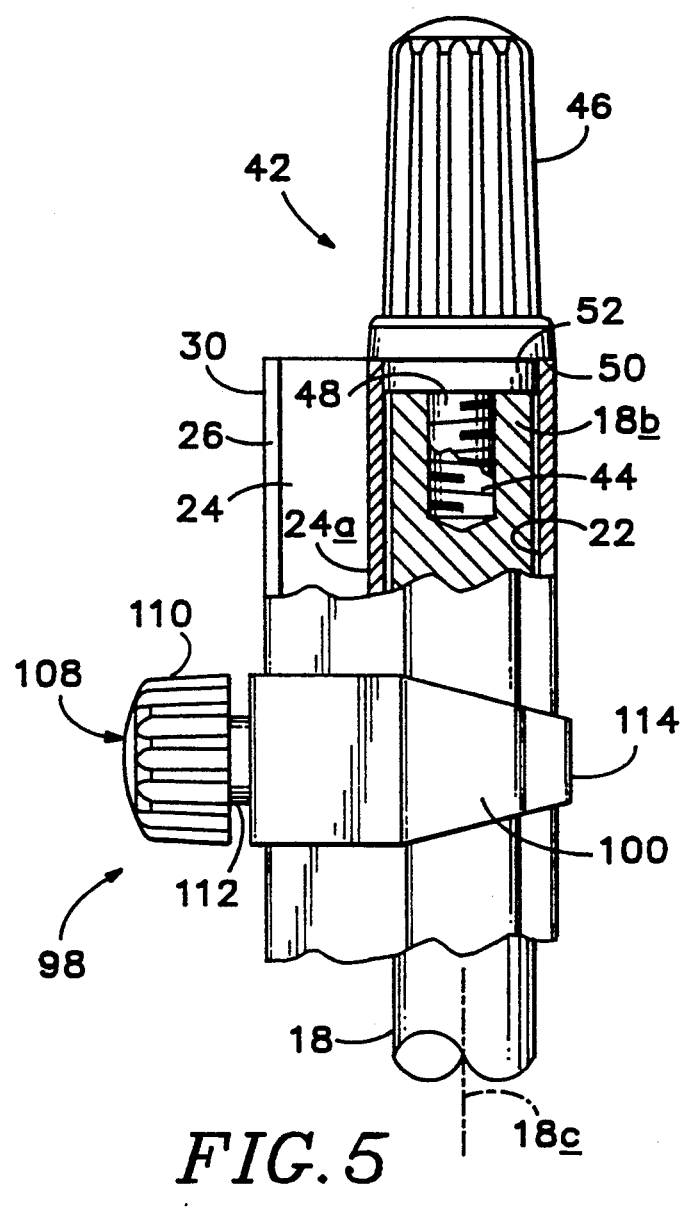
FIG. 5 is an enlarged side elevation of a sleeve locking mechanism of the invention.

Referring momentarily to FIGS. 1, 3 and 5, a sleeve lock mechanism is shown generally at 42. Sleeve lock mechanism 42 includes a threaded receiver 44, formed in the other end 18b of rod 18. A knob 46 has a threaded shaft 48 carried therein which is received in threaded receiver 44, which is centered on rod central axis 18c. Knob 46 further includes a flange 50 which rides on the top of sleeve 20 and a stepped region 52 which is receivable in central bore 22. Sleeve lock mechanism 42 is operable to prevent rotation of sleeve 22 relative to rod 18 by providing a variable coefficient of friction between bushing 34, lower surface 40, and base plate 12, by forcing sleeve 20 downwardly onto bushing 34 and base 12.

Referring again to FIGS. 1, 2 and 3, an arm structure of the invention is depicted generally at 54. Arm structure 54 includes a mounting portion 56, which has a cross section that conforms to the generally rectangular cross section of the inside of channel 24. Mounting portion 56 is vertically, slidably received in channel 24. Mounting portion 56 has a frictioning member 58 located adjacent the upper end thereof, for engagement with the interior rear wall 24a of channel 24. In the preferred embodiment, frictioning member 58 takes the form of a cylindrical plug and is formed of a material which has a relatively high coefficient of friction.

Arm structure 54 further includes a receiver portion 60. Receiver portion 60 has an interior, horizontally extending cavity 62 which receives an extensible portion 64 therein. Extensible portion 64 includes an elongate, vertically extending element 65. Receiver portion 60 includes stop lugs 66 formed therein which are abutted by tabs 68, 70 on extensible portion 64, and which limit the lateral travel of extensible portion 64 relative to receiver portion 60.

Extensible portion 64 includes means for carrying a pressure pad, which in the preferred embodiment, takes the form of a head element 72, located at one end of horizontally extending element 65. head element 72 includes a pad carrying portion 74, which receives a pressure pad 76 thereon by means of a friction fit. A suitable pressure pad for use on clamp 10 is disclosed in U.S. Pat. No. 4,572,182 to Royse. Such a pad includes a notch 78 formed therein to allow easy withdrawal of a catheter from a puncture site with the pad in touching proximity to the puncture site. Pressure pad 76, as depicted, includes an upturned edge 80 which provides a greater radius of curvature 82 adjacent the edge of pad 76, to provide increased patient comfort.

In the preferred embodiment, arm structure 54 includes a number of separate pieces, which are joined together to form the completed structure. Mounting portion 56 and one side of receiver portion 60 may be integrally formed from a single molded piece 84, while the other side of 86 of receiver portion 60 may be joined thereto by fasteners such as screws 88. A web 90 extends between mounting portion 56 and one side 84 of receiver portion 60 and rides in slot 26.

A releasing lever 92 is pivotally mounted on a pin 94 formed in the top of mounting portion 56. A camming surface 96 is located adjacent pin 94 and is operable to release a friction engagement between mounting portion 56 and the interior of channel 24 when it is desired to release the pressure on pressure pad 76. Releasing lever 92 extends outwardly through slot 26 along the top of receiver portion 60.

Although the arrangement of mounting portion 56 and frictioning member 58 is adequate to maintain the vertical position of arm structure 54 in normal usage, it is sometimes desirable to lock the arm structure in a position where it is prevented from raising in the vertical plane, and/or to be able to keep a record of the height of arm structure 54 as such height is changed during the course of the procedure. To this end, an arm lock 98 is provided.

Arm lock 98 includes a surrounding structure 100 which is clearance fit about sleeve 20, encompassing the entire sleeve. Structure 100 is vertically, non-rotatably slidable on sleeve 20. Surrounding structure 100 includes an engagement portion 102, which is inserted into, and received in, channel 24 and which contacts the interior surface 28a, 30a, of each flange 28, 30 respectively. Engagement portion 102 includes a threaded in a face of surrounding structure 100. A locking mechanism 108 includes a knurled knob 110 and a friction structure 112, wherein the friction structure is received in bore 106 and contacts the exterior surface of each flange. This arrangement, when knob 110 is tightened, forces engagement portion 102 into a non-sliding frictional engagement with the interior surface of the flanges surrounding slot 26.

The surface of surrounding structure 100, indicated at 114, may be provided with suitable indicia, such as an arrow and a legend which indicates whether the index plate 32 is read at the top or bottom of surface 114.

As previously noted, it may be desireable, during extended procedures, to gradually release the pressure applied by artery clamp 10. Surrounding structure may be moved by a predetermined amount at set intervals, which predetermined amount is indicated by the graduations on index plate 32 as read at surface 114.

OPERATION

Near the end of a catheterization procedure, artery clamp 10 is positioned proximate to the catheterization puncture site. Base 12 is positioned under the patient's thigh, or possibly under a mattress pad on which the patient is lying. With sleeve lock mechanism 42 in a loose condition, sleeve 20 and arm structure 54 are rotated relative to base 12, as indicated by arrows 116 and 118. Simultaneously therewith, extensible portion 64 and head element 72 are moved laterally relative to sleeve 20, as indicated by arrow 120, to position pad 76 over the puncture site, with notch 78 over the catheter as it projects from the puncture site. Arm structure 54 may be lowered to be in contact with the patient's skin. As the catheter is withdrawn, the medical technician applies pressure to the puncture site with pad 76 by exerting a downward force on arm structure 54 as close to sleeve 20 as possible. This causes pad 76 to exert pressure against the puncture site. As the medical technician releases pressure on arm structure 54, the upward pressure against pad 76 causes the arm structure to lock in position within channel 24. After pad 74 has been pressed against an artery to compress it, the resulting upward pressure against the pad causes mounting portion 56 to tilt within channel 24. Specifically, a high-frictioning engagement takes place between opposite interior sides of channel 24 and mounting portion 56, with frictioning member 58 providing most of the contact against the rear interior wall of channel 24. The arm structure will remain in this position without further assistance. As previously noted, it may be desireable to bring arm lock 98 to bear on top of arm structure 54 to provide an indication of the relative position of arm structure 54 to sleeve 20, as referenced by index plate 32.

To release arm structure 54, arm lock 98 is raised substantially above the level of arm structure 54, if the arm lock has been positioned to hold arm structure 54 in place. The medical technician may then raise releasing lever 92, which results in camming surface 96 contacting the rear interior wall 24a of channel 24 which releases mounting portion 56 from its frictional engagement with channel 24, thereby allowing the arm structure to be raised upwardly.

If it is desired to move arm structure 54 upwardly a slight amount, as perhaps under the control of arm lock 98, the arm lock is released and raised to its next desired position. Downward pressure may then be exerted on head element 72 with simultaneous upward pressure applied to the underside of arm structure 54, close to sleeve 20. Arm structure 54 is then moved upward until it contacts arm lock 98. This action results in decreased pressure from pressure pad 76 over the puncture site.

Although a preferred embodiment of the invention has been disclosed herein, it should be appreciated that variations and modifications may be made thereto without departing from the scope of the invention as defined in the appended claims.

INDUSTRIAL APPLICABILITY

The artery clamp is useful in the medical arts where it is necessary to maintain pressure on a puncture site for an extended period of time.

What we claim is:

1. An improved artery clamp comprising:
   a pressure pad (76);
   a base (12);
   an elongate rod (18) having one end (18a) thereof mounted on said base (12) normal thereto;
   an elongate sleeve (20) having a central bore (22) and a channel (24) extending the length thereof, said rod (18) being received in said central bore (22) to allow rotation of said sleeve relative to said rod, said channel (24) having an axially extending slot (26) along at least a portion of its length; and
   an arm structure (54) extending laterally outwardly from said sleeve (20), said arm structure (54) including a mounting portion (56) which receivable in said channel (24) and vertically slidable along the length thereof, a receiver portion (60) attached to said mounting portion (56), and an extensible portion (64) which is received in said receiver portion (60) and is laterally adjustable relative thereto, said extensible portion (64) including means (72) for carrying said pressure pad (76) thereon.

2. The improved artery clamp of claim 1 wherein said base (12) is a generally planar structure and which has a bore (16) adjacent one side (12a) thereof, and wherein said rod (18) is fixed in said bore (16).

3. The improved artery clamp of claim 1 which further includes a bushing (34) which is interposed between said sleeve (20) and said base (12) and which has a sleeve-receiving region (36) for receiving one end (20a) of said sleeve (20) therein, and a bore (38) extending through the bottom thereof sized to allow passage around said rod (18), and a flat lower surface (40) constructed and arranged to contact said base (12).

4. The improved artery clamp of claim 1 which includes a sleeve lock (42) to prevent rotation of said sleeve (20) relative to said base (12), said rod (18) having a threaded receiver (44) at the other end (18b) thereof, said sleeve lock (42) including a knob (46) having a threaded shaft (48) carried therein for reception in said threaded receiver (44), said sleeve lock (42) frictionally engaging said sleeve (20) to prevent rotation thereof.

5. The improved artery clamp of claim 1 wherein said sleeve (20) includes an index plate (32) thereon on the side of said sleeve (20) opposite said slot (26) for indexing the vertical position of said arm structure (54).

6. The improved artery clamp of claim 1 wherein said channel (24) has a generally rectangular cross section and includes a pair of spaced flanges (28, 30) surrounding said slot (26), each flange (28, 30) having an interior surface (28a, 30a) and an exterior surface (28b, 30b), and which further includes an arm lock (98) for maintaining said arm structure (54) below a specific level on said sleeve (20), said arm lock (98) including a surrounding structure (100) which encompasses said sleeve (20) and is vertically slidable thereon, and a locking mechanism (108) for locking said surrounding structure (100) in a desired location.

7. The improved artery clamp of claim 6 wherein said surrounding structure (100) includes an engagement portion (102) which is inserted into said channel (24) and which contacts the interior surface (28a, 30a) of each flange (28, 30) and wherein said locking mechanism (108) includes a friction structure (112) which contacts the exterior surface (28b, 30b) of each flange (28, 30) thereby forcing said engagement portion (102) into non-sliding, frictional engagement with the interior surface (28a, 30a) of said flanges (28, 30).

8. The improved artery clamp of claim 1 wherein said arm structure receiver portion (60) is integrally formed with said mounting portion (56) and has an interior horizontally extending cavity (62) which receives said extensible portion (64).

9. The improved artery clamp of claim 8 wherein said cavity (62) has stop lugs (66) formed therein and said extensible portion (64) has tabs (68, 70) which abut said stop lugs (66) to limit lateral travel of said extensible portion (64) relative to said receiver portion (60).

10. An improved artery clamp comprising:
    a pressure pad (76);
    a generally planar base (12);
    an elongate rod (18) having one end (18a) thereof mounted on said base (12) normal thereto;
    an elongate sleeve (20) having a central bore (22) and a channel (24) extending the length thereof, said rod (18) being received in said central bore (22) to allow rotation of said sleeve (20) relative to said rod (18), said channel having an axially extending slot (26) along at least a portion of its length, wherein said channel (24) has a generally rectangular cross section and includes a pair of spaced flanges (28, 30) surrounding said slot, each flange having an interior surface (28a, 30a) and an exterior surface (28b, 30b); and an arm structure (54) extending laterally outwardly from said sleeve (20), said arm structure (54) including a mounting portion (56) which is receivable in said channel (24) and vertically slidable along the length thereof, a receiver portion (60) attached to said mounting portion (56), and an extensible portion (64) which is received in said receiver portion (60) for limited lateral length adjustment relative thereto, said extensible portion (64) including means (72) for carrying said pressure pad (76) thereon; and an arm lock (98) for maintaining said arm structure (54) below a specific level on said sleeve (20), said arm lock (98) including a surrounding structure (100), which encompasses said sleeve (20) and is vertically non-rotatably slidable thereon, and a locking mechanism (108) for locking said surrounding structure (100) in a desired location.

11. The improved artery clamp of claim 10 wherein said base (12) has a bore (16) adjacent one side (20a) thereof, and wherein said rod (18) is fixed in said bore.

12. The improved artery clamp of claim 10 which further includes a bushing (34) which is interposed between said sleeve (20) and said base (12) and which has a sleeve-receiving region (36) for receiving one end (20a) of said sleeve (20) therein, and a bore (38) extending through the bottom thereof sized to allow passage around said rod (18), and a flat lower surface (40) constructed and arranged to contact said base (12), wherein said bushing (34) is rotatable with said sleeve (20) relative to said base (12).

13. The improved artery clamp of claim 10 which includes a sleeve lock (42) to prevent rotation of said sleeve (20) relative to said base (12), said rod (18) having a threaded receiver (44) at the other end thereof extending axially along the central axis (18c) of said rod (18), said sleeve lock (42) including a knob (46) having a threaded shaft (48) carried therein for reception in said threaded receiver (44), said sleeve lock (42) frictionally engaging said sleeve (20) to prevent rotation thereof.

14. The improved artery clamp of claim 10 wherein said sleeve (20) includes an index plate (32) thereon on the side of said sleeve (20) opposite said slot (26) for indexing the vertical position of said arm structure (54).

15. The improved artery clamp of claim 10 wherein said surrounding structure (100) includes an engagement portion (102) which is inserted into said channel (24) and which contacts the interior surface (28a, 30a) of each flange (28, 30) and wherein said locking mechanism (108) includes a friction structure (112) which contacts the exterior surface (28a, 30a) of each flange thereby forcing said engagement portion (102) into non-sliding, frictional (28,30). engagement with the interior surface (28a, 30a) of said flanges 16. The improved artery clamp of claim 10 wherein said arm structure receiver portion (60) is integrally formed with said mounting portion (56) and has an interior horizontally extending cavity (62) which receives said extensible portion (64), wherein said cavity has stop lugs (66) formed therein and said extensible portion (64) has tabs (68, 70) which abut said stop lugs (66) to limit lateral travel of said extensible portion (64) relative to said receiver portion (60).

* * * * *